United States Patent [19]
Jansen et al.

[11] Patent Number: 5,800,527
[45] Date of Patent: Sep. 1, 1998

[54] SUPPORT HOUSING FOR VALVE AND CLOSURE MEMBERS, IN PARTICULAR FOR HEART VALVE PROSTHESES

[75] Inventors: Josef Jansen, Aachen; Ulrich Jansen, Dusseldorf, both of Germany

[73] Assignee: Adiam Medizintechnik GmbH & Co. KG, Germany

[21] Appl. No.: 367,298
[22] PCT Filed: Jul. 9, 1993
[86] PCT No.: PCT/EP93/01794
   § 371 Date: Jan. 6, 1996
   § 102(e) Date: Jan. 6, 1996
[87] PCT Pub. No.: WO94/01060
   PCT Pub. Date: Jan. 20, 1994

[30] Foreign Application Priority Data
Jul. 10, 1992 [DE] Germany .................. 42 22 610.4

[51] Int. Cl.⁶ ............................................ A61F 2/24
[52] U.S. Cl. ..................................... 623/2; 623/900
[58] Field of Search ........................... 623/2, 900

[56] References Cited

U.S. PATENT DOCUMENTS 4,441,216  4/1984  Ionescu et al. .................. 623/2

FOREIGN PATENT DOCUMENTS 0528094  11/1976  U.S.S.R. ........................ 623/2
1116573  7/1985  U.S.S.R. ........................ 623/2

*Primary Examiner*—David H. Willse
*Attorney, Agent, or Firm*—Harness, Dickey & Pierce, P.L.C.

[57] ABSTRACT

A support housing (1) for valve and closure members, in particular for heart valve prostheses, has a base ring (2) which carries at least two symmetrically offset posts (4/5) substantially oriented in the direction of the ring axis and linked together by curved strips (3) for securing at least two flexible webs (6/7). In order to produce with such a support housing a valve or closure member, in particular a heart valve prosthesis, which operates reliably even with different closing pressure differentials, i.e. in particular even under varying physiological stress conditions, the stent (1) is only retained in sections and with limited flexibility. For that purpose the free ends (4) of the posts have a rigid form, and/or the bases of the posts have a flexibility limited by stops, and/or the strips (3) have a flexibility limited by stops.

41 Claims, 2 Drawing Sheets

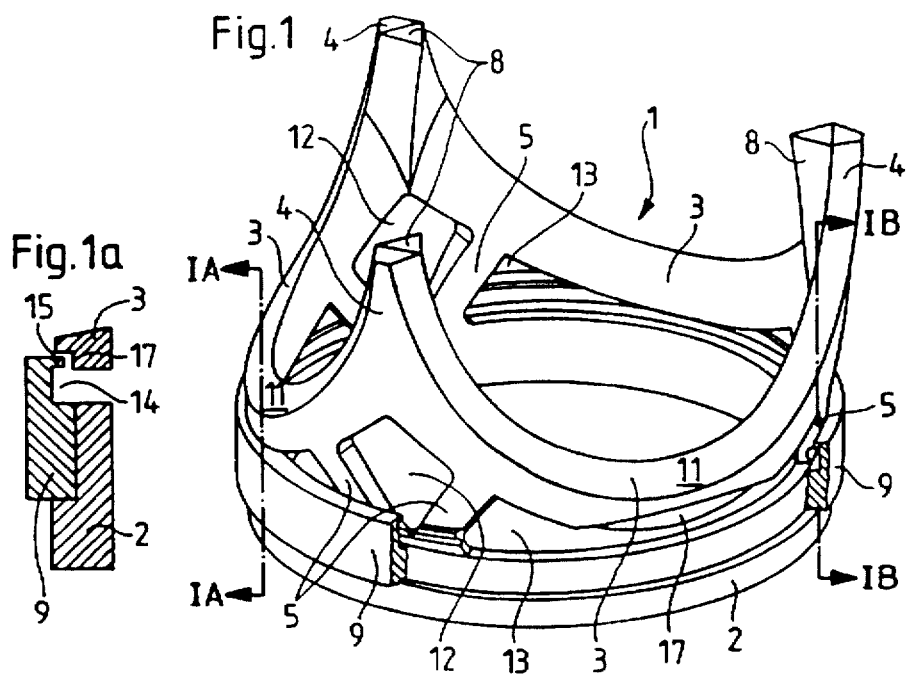
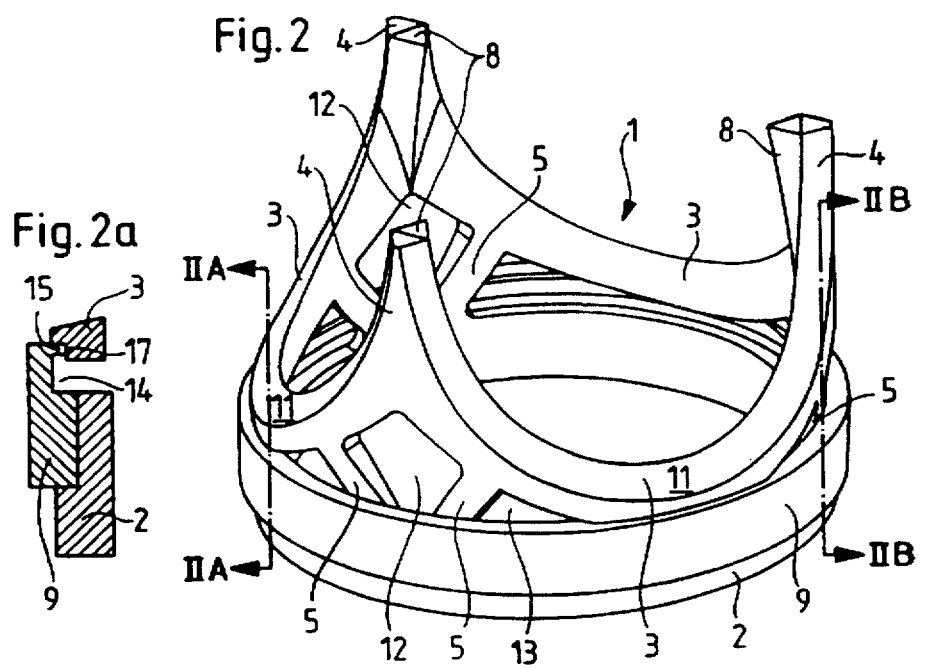
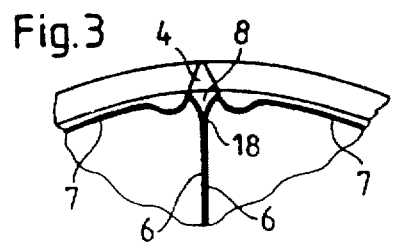

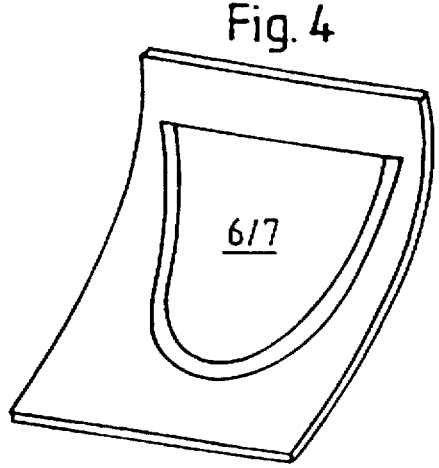
Fig. 4
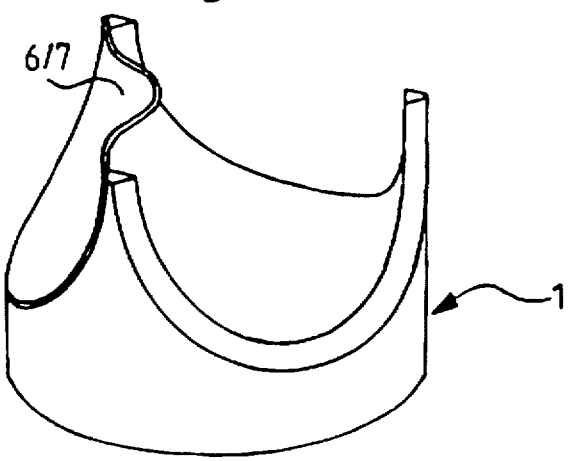
Fig. 5
Fig. 6
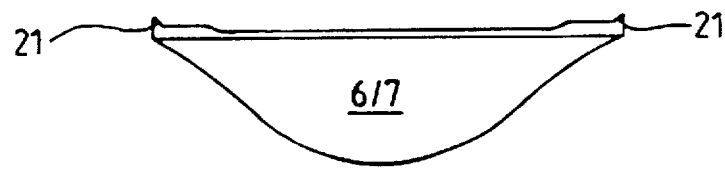
Fig. 7
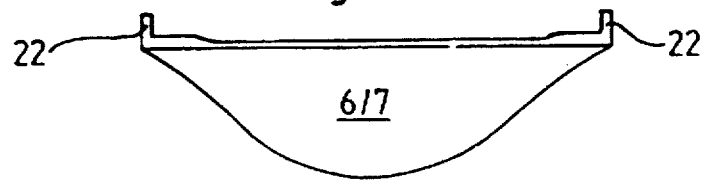
Fig. 8
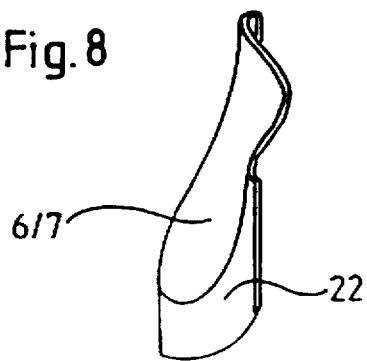

5,800,527

SUPPORT HOUSING FOR VALVE AND CLOSURE MEMBERS, IN PARTICULAR FOR HEART VALVE PROSTHESES

TECHNICAL FIELD

The invention relates to a support housing (stent) for valve and closure members, in particular for heart valve prostheses, having a base ring which carries at least two symmetrically offset posts substantially oriented in the direction of the ring axis and linked together by curved strips for securing at least two flexible webs.

One of the main problems in forming a prosthesis from a stent of this kind is to provide a suitable construction in which the stent posts can be deformed in the implanted state by very small forces or closing pressure differentials in the bloodstream from the form in which they are manufactured or from some other, possibly conical, initial form into a cylindrical state, after which a radially inwardly directed deformation of the stent posts can only take place by the application of large forces.

For better understanding, the closing behaviour and the opening movement of the natural aortic valve will be described. In the natural aortic valve the webs form an integral part of a hose-shaped structure, the aortic root. Adjoining the webs there are hollows in the walls of the aorta, the aortic bulbs. In the case of a prosthesis this is called in the literature an "unstented" valve or conduit valve implant (often without bulbs), in contrast to the stent valves described here. For closure, i.e. in the closed position of the webs, these aortic bulbs serve to provide mechanical strengthening. Without the hollows of the bulbs the aortic valve would not be able to absorb radial components of force in order to counterbalance the forces exerted on it by the webs under diastolic pressure. In artificial stent heart valves these components of force are absorbed by their stent posts, which are thereby deformed radially towards the middle of the valve.

The differences in construction of the stented and unstented valves result in different movement or opening behaviour of the web-like closure elements.

In the unstented valve with bulbs the commissures (in the case of a stent valve the tips of the posts) of the webs are firmly connected to the aortic root. Because of the ability of the aortic root to expand the natural valve can open prematurely. At the start of the systole the ventricular pressure increases through the isovolumetric contraction, so that the commissures move radially outwards. This commissure expansion begins even before the valve opening proper. The movement of the commissures gives rise to a force acting tangentially on the web. Thereby the curvature of the web is decreased, the webs gradually separate from one another, and they are drawn into an open position. The very small amount of valve opening brought about in this way can be recognised without any detectable forward flow and in the absence of any increase in aortic pressure. In the course of the systole the expansion of the aortic root further increases as the aortic pressure increases. In systole the aortic valve thus forms a tube with increasing diameter and, from the point of view of hydrodynamics, a diffuser. Besides this, the ability of the bulb valve to expand serves as it were to regulate the web overlap area in the closed state and thus prevents folding within the web under varying physiological load conditions, i.e. different closing pressure differentials. If one considers the web of the natural valve in the closed position at different pressure differentials, with increasing maximum pressure differential across the valve the aortic pressure, and thereby also the diameter of the aorta at the position of the commissures, increases at the same time. As a result the valve webs lift downstream. Through these actions the area of web overlap decreases. The bulb valve obviously adapts to different load conditions through variation in web overlap areas.

PRIOR ART

From the prior art, e.g. from DE 38 34 545 A1 and DE 38 90 571 T1, stents are known which have a cylindrical base ring which is prolonged by three posts each offset circumferentially by 120° and narrowing in the axial direction. The bays formed by the posts, which resemble a trifurcate crown, serve to receive the webs which perform the closing function proper of the valve. The bays differ geometrically from one prosthesis to another but often reproduce the geometrical form of the lines of attachment of the natural valve web to the aortic wall. The webs closed under closing pressure cause the more or less elastic stent posts to bend radially inwards towards the axis of the valve. In this connection the second of these known proposals seeks to obtain the greatest possible flexibility through a composite polymer and spring steel construction of the posts and through apertures in their foot region.

The known stent valve constructions have the disadvantage that these valves are not sufficiently adaptable to varying physiological load conditions, i.e. different closing pressure differentials. By the closing pressure differentials in the closed state of the valve radial components of force are exerted through the webs on the stent posts, which are thereby deformed radially towards the middle of the valve. As the closing pressure differential increases the webs sink upstream, bulge inwards and come to meet along their free edges until complete web overlap seals off the valve. Since a stent valve can only be designed in a constructionally advantageous manner for one closing pressure, at pressure differentials further increased above this state the radial movements of the posts, the bulging of the webs and the overlapping of the webs further increase. At the level of the free edge of the web the area of overlap becomes excessively large, so that undesired folds form in the web. In addition, this effect is reinforced on the one hand by the desired flexible behaviour described below, and on the other hand by creep of the stent posts.

To reduce high stresses in the regions of the web (commissures) which adjoin the stent tips, it has been proposed, e.g. in DE 35 41 478 A1 and U.S. Pat. No. 5,037,434, to construct the stent posts so that they are very flexible in their upper part. If, however, as is usual in the prior art, the stent posts or tips are flexible, they become disproportionately elongated at these positions on being loaded with the closing pressure differential, which ultimately leads to creep and thereby to premature fatigue.

It is therefore necessary, in the case of stent valves, to limit the deformation of the stent posts, in particular of their tips, radially inwardly towards the axis of the valve when the webs are in the closed position. While a rigid stent would reduce the sinking of the webs and the folding, it would not dampen the steep gradients of pressure with time, dp/dt, on closing the valve.

THE INVENTION

The object of the invention is therefore to provide a support housing of the kind referred to above by means of which a valve or closure member, in particular a heart valve prosthesis, can be produced which operates reliably even with differing closing pressure differentials, i.e. in particular even under varying physiological load conditions. The invention is based on the idea of producing by structural means a marked, progressive closing pressure/post deformation characteristic, such that on the one hand at high closing pressure differentials the deformation of the posts is limited up to defined positions and on the other hand stress concentrations in the posts and webs are avoided.

The invention achieves this object by the basic concept of only making the stent flexible in certain regions and to a limited extent, and by this means achieves substantially better opening and closing properties. Within the scope of the invention two alternative constructions which may be used are proposed, each of which in itself achieves the object, while both can be used in combination, which represents an optimised solution. The first alternative consists in making the free ends of the posts rigid, in particular by an accumulation of material on the free ends of the posts, which are preferably formed so as to achieve a post cross-section which, together with the curved strips provides, in distinction to the state of the art, an outwardly directed surface for securing the webs which is only singly curved, in consequence of which this first alternative surprisingly brings with it the additional advantage of enabling a flat web to be joined in a form-fitting way to a singly curved surface. The relative rigidity of the stent posts in the upper region avoids high elongations there which in the case of previously known stents of plastics material have led to increased creep. The accumulation of material in the form of a prismatic inner overlay on the post ends leads in addition in a simple manner to the result that the webs attached to the singly curved post and strip surfaces—the connection of the webs to the stent can be by adhesion or welding—lie sealingly on the inner overlay without the need for additional sealing measures which would otherwise have been necessary on account of the outwardly directed securing surfaces which result from the trapeziform post cross-section with the shorter side of the trapezium directed outwards.

Specific embodiments and the advantages thereof will appear from the claims and the following description.

In the second alternative solution the invention contemplates a stop-limited flexibility of the bases of the posts, optionally replaced, but preferably supplemented, by a stop-limited flexibility of the strips such that radial displacement or deformation of the posts is possible, which is then limited by a stop, which in the combination with the first alternative, as well as the optimisation of properties referred to, also makes structural adaptation to the most varied requirements possible.

The stop-limited flexibility of the posts and of the strips connecting them, which are preferably formed integrally therewith, the posts for their part having apertures in their base region, is generally achieved by mechanical shaping means, in the form of a kind of tongue and groove stop. For this purpose an additional ring (stop ring) is provided in the base region, preferably with a circumferential groove into which outwardly directed lug-like projections or circumferential radial lips which are attached to the posts in the base region thereof engage, while the strips have in their region near the base, i.e. in each case intermediate two posts, a recess on the underside which is adapted to the cross-sectional shape of the stop ring and is preferably rectangular, which in the initial state, i.e. the state in which the posts are not deformed inwardly, but rather are optionally in any event slightly inclined outwards, is spaced from the stop ring, just as the above-mentioned ribs on the feet of the posts are spaced from the groove in the stop ring.

The arrangement is selected to be such that the groove in the stop ring is at a level which permits the upper rim of the groove to serve on the outside as a stop for the strips and on the inside as a stop for the post ribs. This ensures that the inwardly directed deforming movement of the posts is stopped on reaching the desired end position by the ribs, which are then inside the groove, coming to bear on the stop ring. Optimally this is supported by the fact that as this movement occurs, at the same time as the ribs are stopped, in the region of the strips, through the recess in the strip likewise becoming seated on or coming to bear against the stop ring, the outwardly directed movement of the connecting strip also leads to a limitation of movement of this flexible part of the stent. Within the scope of the invention it is also possible, if stepped flexibility properties are desired, to allow the stopping to take place in a temporally offset manner: this can be done by different spacings of the mutually associated stop surfaces.

The heart valve stent should, in the as-manufactured state, have the shape of a diffuser. A conical form with a conical angle between 2° and 14° is preferred.

To limit the contraction of the stent posts it is now proposed, in accordance with the invention, to place an additional ring above the base ring. Through the webs, the closing pressure of the blood exerts forces directed radially towards the middle of the valve on the stent posts, and contracts them. Since the segments in the post region are relatively rigid the closing forces are mainly diverted into a deformation of the region of the strips near the base—hereinafter also referred to as segment bows. The segment base regions are deformed and displaced simultaneously radially outwards and upstream, until further deformation is limited by the inserted ring, as can be seen in particular from the enlarged sections in FIGS. 1 and 2. By the contraction of the stent posts the V-stays are also bent at the same time, particularly in the thin-walled, flexible connecting region to the base ring. To this extent what is involved is technically a film hinge. The stop is preferably designed so that the stent posts are deformed into a cylindrical configuration. With increasing closing pressure differential the further contraction then depends essentially on the cross-sectional shape and the modulus of elasticity of the stent post. The stent posts are, however, made relatively rigid. With this constructional design there is expansibility and more or less limited contractibility of the stent posts. The grid structure, together with the limitation of deformation through the stop ring, distributes the load of the closing pressure over the whole length of the segments and thus avoids stress concentrations such as occur in the case of stents commonly used hitherto.

The "stop" formed by the inserted ring could also be integrated directly in the base ring, i.e. stop ring and base ring could be a single component made of the same material. In the event that the openings in the stent wall are filled with a material of lower modulus of elasticity the filler material would lead to a damping of the contraction of the stent.

Alternatively or in addition to the limitation of deformation of the segment base region, a direct limiting of the post bending in the region of the connecting stay is preferably contemplated. For this purpose the stay is provided in the circumferential direction with a rib-like projection, over which a kind of (snap) hook is brought from the base ring which restricts the rotation towards the tip of the stent of the projections or of the film hinge formed by the stay brought about by the closing pressure. Thus the force form-fitting connection depends on the interlocking of undercuts, on the projection on the connecting stays on the one hand and on the hook proceeding from the base ring on the other hand.

The constructional design of the posts and the selection of material are dimensioned such that the limit of the contractibility of the stent posts in the cylindrical state is preferably reached at pressure differences of 2 to 30 mm Hg. With closing pressures in excess of this the stent behaves predominantly rigidly, i.e. further contraction of the crown of the stent is prevented. The valve can thereby adapt to a larger range of closing pressure differentials, and the undesired further bulging and folding of the web as described above be reduced.

If on the other hand the pressure differential decreases towards zero the expansion of the stent causes premature opening of the web. The post expansion already begins before the valve opening proper. The movement of the posts gives rise to a force acting tangentially on the web, in particular on the commissures. The curvature of the web is thereby decreased, the webs gradually become separated from one another, and they are drawn into an open position. The increase in the bending radii of the opening webs decreases the stresses in the webs and thus avoids stress concentrations. Moreover during the opening phase the stent forms a tube of increasing diameter for which, from the point of view of hydrodynamics, it forms a good diffuser.

A detail of the construction of the stent of the invention is formed by the surfaces of the bow-shaped bays of the crown, i.e. of the strips to which the webs are fastened. The line of connection of web and stent, i.e. the bow-shaped bay, is that obtained by penetration of, for example, a sphere through a tubular stent. The lines of connection can alternatively be obtained by penetration by any other geometrical body so that the bow-shaped bays result. These surfaces are usually doubly curved. In the type described here the bay surfaces are, in contrast to the prior art, singly curved, so that the normals to these surfaces point radially towards the valve axis. The characteristic cross-sectional shape of the tips of the stent posts is thereby trapeziform to triangular with, in contrast to the usual forms, the shorter of the parallel sides of the trapezium, pointing radially outwards, as can be seen from FIGS. 1 and 2. The transition from the singly curved surface of the bay to the outer cylindrical surface of the stent can also be slightly rounded or bevelled with a bezel.

If the webs are secured along the line of penetration at the inner diameter of the stent, this trapeziform shape results in particular in a useful, radial guidance of flow around the stent posts. The undercuts such as are caused by oppositely directed trapeziform shapes of stent posts otherwise generally used are dispensed with.

The triangular backflow gaps on the internal diameter at the stent tips resulting from the arrangement of the widths of the parallel sides of the trapezium are closed by the internal overlays or extensions in accordance with the invention, which extend beyond the point of attachment of web to stent in the direction of the middle of the valve. In the plan view the extending nose has a triangular shape with concave tapering on both sides. Starting from the point of connection of the web to the stent, the cross-section of the post thus first of all tapers in a straight line or in the form of a triangle or convexly and then concavely. If the triangular tapering takes place at very acute angles, the subsequent concave tapering can be dispensed with. Downwards, i.e. in the upstream direction, the nose tapers into the stent wall up to the start of the segment end connections.

The inner overlay in accordance with the invention relieves the regions of the web commissures of stress in the closed state and steers them gradually round at smaller angles, until the webs are directly against one another. High stress concentrations which, in the case of other usual forms of valve, occur in the web commissures, are thus avoided. Consequently a further advantage is achieved by the inner overlays which adjoin the segment end connection, in addition to the stiffening of the apexes of the crown which is an object of the invention.

The advantages of this nose-shaped stent tip are also obtained if the stent wall has no apertures in it, or if the surfaces of the bays deviate from the singly curved form.

The preceding remarks also apply with regard to the advantage achieved by the stent of the invention in the same way for a valve with two, three or more webs.

If a stent having a form such as that described above is integrated in a cylindrical hose, or is made in addition with so-called bulbs (sinus valsalvae), like the natural aortic valve, such a valve prosthesis can be used in artificial blood pumps or as a conduit valve implant as a replacement for damaged aortic valves.

BRIEF DESCRIPTION OF THE DRAWINGS

FIG. 1 is a perspective view of the invention in which the posts of the stent are inclined slightly outwards.

FIG. 1a is a cross-sectional view along IA—IA of FIG. 1.

FIG. 1b is a cross-sectional view along IB—IB of FIG. 1.

FIG. 2 is a perspective view of the invention in the cylindrical state with the attached webs closed under a closing pressure.

FIG. 2a is a cross-sectional view along IIA—IIA of FIG. 2.

FIG. 2b is a cross-sectional view along IIB—IIB of FIG. 2.

FIG. 3 is a partial plan view from above of a stent apex.

FIG. 4 is a perspective view of a flat blank from which a web is cut.

FIG. 5 is a perspective view of the securement of the web to the stent.

FIG. 6 is a plan view from above of the free upper edge of the web.

FIG. 7 is a plan view from above of the free upper edge of the web of another embodiment.

FIG. 8 is a perspective side view showing the web of FIG. 7 in the joined state.

The invention will now be described in more detail by way of example with reference to the drawings.

As manufactured, a component of the flexible heart valve stent, indicated generally by 1, as shown in particular in the perspective views in FIGS. 1 and 2, comprises a cylindrical base ring 2 to receive a suture ring required for the implantation, which is not shown since it is well known. A further component of the stent as manufactured is a kind of trifurcate, wire-shaped crown which consists of three segment bows or even strips 3, which merge at their free ends in common apexes of the crown or post ends 4, beneath which V-shaped stays 5 proceed from the segment bows or strips, which are optionally integrally combined with the base ring 2, so that a very flexible structure results, since the connection of the posts and strips or of the trifurcate "crown" 3, 4 takes place merely by way of these stays 5.

The securing of the closure elements proper, namely the webs 6/7, to the stent takes place along the obliquely outwardly facing surface of the segment bows 3 and of the post ends 4. The V-stays 5, like the post ends 4, which thus together replace the posts of conventional designs, are arranged offset by 120°, and consequently represent posts having apertures in them near the base, so that in this way, too, great flexibility is provided in the base region, just as is also provided for the segment bows in the absence of a direct connection with the base ring in this region. In contrast, the strips or segment bows 3 are of relatively rigid construction in the region of the post ends 4. This purpose is also served by an inner overlay 8, already described in detail above, in the region of the post ends 4, namely a prismatic inner overlay 8 of triangular cross-section, which has one side of the triangle adjoining the inner surface of the post ends 4. The regions of the V-stays 5, together with the parts of the segments adjoining the crown apexes or the post ends 4, are thus to be regarded as stent posts.

Since, as already mentioned, the base region of the segment bows or strips 3 is not connected to the base ring 2, the greatest possible flexibility, i.e. contraction of the stent posts under very small closing pressures, is achieved. The apertures in the grid-shaped stent wall are filled or covered with a material which has a substantially lower modulus of elasticity compared with the other components of the stent. This seals the stent wall against radial through-flow. Optionally the apertures can also be closed by means of the stent material itself, provided the thickness in these regions to be covered is substantially smaller than that of the segment bows or strips 3. Finally, the stent in accordance with the invention also includes a coaxial stop ring 9 placed partly around the base ring 2, which takes care of the desired limitation of movement of the stent posts in the manner which has previously been described and which will be further explained below with reference to the drawings.

In detail, the accompanying drawings show:

MODES OF PRACTICING THE INVENTION

FIG. 1 represents a perspective view of a stent in accordance with the invention in the as-manufactured diffuser shape, i.e. with posts inclined slightly outwards. The stop ring 9 placed coaxially partly round the base ring 2 and held in position thereon is shown partly broken through in the front region, in order to make clear its cross-section and its spatial relationship to the other parts of the stent, as can also be seen from the cross-sections from FIG. 1 shown in FIGS. 1a and 1b. This arrangement and form of stent correspond to the open position with webs (not shown) fitted, which would then be connected to the outwardly inclined, continuous, singly curved surfaces of the strips 3 and post ends 4. The end connections of the segment bows or strips 3 form the apexes of the "crown" or post ends 4.

The surfaces 11 mentioned are singly curved, resulting in trapeziform sections of the post ends, the shorter of the parallel sides of the trapezium facing outwards, whereas in the prior art a triangular form with an inwardly projecting apex is provided in this position. The "crown" shape with the V-shaped stays 5 connected at the end to the base ring results in a grid-shaped stent wall with apertures 12 and 13, of which the aperture 12 can optionally also be dispensed with. For the proper functioning of the valve these apertures 12 and 13 must be covered over or filled in in order to avoid undesired backflows. As mentioned, the region of the V-shaped stays 5 and the segment portions adjoining the apexes of the "crown" here forms part of the stent posts.

As can be seen from FIGS. 1a and 1b and 2a and 2b, the stop ring 9 has a circumferential groove 14 running round its inner side at a height such that it is bounded at the top by a kind of rib 15, which forms part of the stop ring and likewise for manufacturing reasons preferably runs circumferentially. Not least on account of the stays 5, which in the initial position shown in FIG. 1 are inclined slightly outwards (see in particular FIG. 1b) the rib is slightly set back relative to the inside wall of the stop ring 9, so that the outward inclination of the stay 5 is not impaired.

As shown by FIGS. 1b and 2b, in the region of overlap with the stop ring 9 the V-shaped stays 5 are provided on the outer side with a preferably circumferential lug-like projection or with circumferential radial lips 16, which are located at the level of the groove 14 and engage freely movably therein in such a way that in the initial state shown in FIG. 1b they do not touch the upper rim of the groove or the rib 15, but in the inwardly bent final state of the posts as shown in FIG. 2b they bear against the rib 15 from below, so that the rib acts as a stop to limit the inward deformation of the "crown".

In the preferred embodiment a corresponding stop is also provided for the region of the segment bows or strips 3 near to the base, as to which reference is made to FIGS. 1a and 2a. For this purpose the segment bows or strips 3 each have at least one rectangular recess 17 in the region near the base, which is arranged circumferentially so as to permit the association shown in FIGS. 1a and 2a, namely not touching the upper rim of the groove or the rib 15 in the widened initial state of the stent, but in the state shown in FIG. 2, i.e. the state with the valve closed, bearing from outside against the rim of the groove or the rib 15 as a stop (see FIG. 2a).

Around the stop ring 9 would be fixed the suture ring (not shown) to be used to sew the valve unit in the natural annulus tissue.

FIG. 2 shows, as already mentioned, the form of stent in accordance with the invention shown in FIG. 1, likewise viewed in perspective, but in the cylindrical state with the attached webs closed under closing pressure, the webs being omitted from the drawing for the sake of clarity. Through the contraction of the stent posts the base region of the segment bows or strips 3 has been deformed upstream and radially outwards and, through the recess 17 on the outside, bears against the stop ring inserted in the base ring, while the lips 16 of the V-stays contact the inside of the upper rim of the groove or the rib 15.

FIG. 3 shows a partial plan view from above of the stent apex, in which in addition the web is shown secured to the backing surfaces 11 inside the segment bows 3, closed at 6 and open at 7. This view clarifies the triangular shape, and concave tapering on each side to the middle of the valve, of the inner overlay 8 of the "crown" apex, whereby a smaller deflection of the closed web is achieved. At the apex 18 of the inner overlay 8 the webs lie one against the other.

Referring now to FIGS. 4 to 8, further particular advantages of the stent in accordance with the invention will be explained, in respect of the form of the webs and their securing to the backing surfaces 11, which is effected by a joining or connecting process, either by adhesion or welding. The preferred process is one in which a substantially flat web is prepared separately from the stent and subsequently secured, by means of adhesion or shrinking, to a stent which has not been spread open or to one which is slightly conical in the as-manufactured state and is not subsequently narrowed by external forces.

The single curvature of the backing surfaces 11, which is achieved by the special trapezium shape of the stent apexes in accordance with the invention, results in a good form-fitting connection of the rims of the webs to the backing surfaces 11.

The webs 6–7 (see FIG. 4) are cut out as substantially flat blanks and, as shown in FIG. 5, are secured to the stent 1 slightly curved, at least at the contact or edge faces. Shaping in this way has the advantage that surfaces at the edge of the webs only have to be deformed very slightly in order to lie on the backing surfaces 11. In addition, because of the single curvature of the backing surfaces 11, a relatively simple holding and pressing tool can be used, which presses the rims of the web on to the stent.

This process, which requires precise positioning of such a small, flexible component as the web, can be simplified if, as shown in FIG. 6, which shows a plan view from above of the free upper edge of the web, there runs along the bent rim of the web, on the inner side oriented towards the stent surfaces, an edge 21, for example triangular, which has a corresponding bevel adapted to the backing surfaces 11. To form the joint the web 6/7 is laid on the stent 1 and is first pressed against the backing surfaces 11 of the stent 1 with a suitable tool, using little force. A small closing pressure is then exerted on the web, which can then quasi "snap in" along its rim, so that joining can then be completed, for example by a welding process.

Another possibility is shown in FIG. 7, wherein the web is prolonged beyond the rims of the backing surfaces 11, in the form of a rim 22 bounding the rounded rim of the web and directed towards its convex surface at an angle to the surface of the web. The edge "enlarged" in this way simplifies the "closing pressure snap fastening process" of attaching the web to the stent. FIG. 8 is a perspective side view showing such a web in the joined state, from which it is clear that the rim 22 merges into the outer surface of the stent or lies sealingly and conformingly thereon, resulting in the said "snap fastening" property.

In a further development three webs can then be made in combination, e.g. as a hose-shaped structure, whereby the form-fitting joining of the web foil to the stent is further simplified.

INDUSTRIAL APPLICATION

The separate production of webs and stent has the advantage of making it possible to make the webs by injection moulding, thus avoiding unfavourably large differences in wall thickness. In addition the production is again considerably simplified in the case of singly curved backing surfaces 11: particularly in the case of individually injection moulded webs the achievement of the tolerance limits of the parts is also considerably improved. A further advantage of the injection moulding technique is that good control of the thickness distribution of the webs can be achieved using injection moulding. The possibility, given by the singly curved backing surfaces which are provided on the basis of the proposal of the invention through the special form and chosen outward inclination of the apexes of the posts, of attaching the inner overlays 8 to avoid backflow gaps when the webs are closed, has the advantage, surprisingly achieved by the invention, that by this additional stiffening of the post ends 4 the stress concentrations in the region of the web commissures are avoided, or at least reduced to a minimum. At the same time the desired flexibility in the lower post region is obtained.

We claim:

1. A support stent for valve and closure members, said stent comprising a base ring, at least two posts mounted on said base ring, said posts extending substantially axially to the direction of a ring axis, said posts having free ends and bases, said bases linked together by curved strips and said posts and said strips having backing surfaces for securing at least two flexible webs thereto, said posts and said strips having outer surfaces and inner surfaces that respectively form outer and inner walls of said stent, said posts being inwardly and outwardly deflectable relative to said base ring with said free ends of said posts being rigid, and stop means for limiting inward and outward deflection of said posts.

2. A stent according to claim 1, wherein said stop means is adjacent to said base ring.

3. A support stent according to claim 1 wherein, said posts having a prismatic inner overlay on said free ends.

4. A stent according to claim 3, wherein said inner overlay has a triangular cross-section tapering concavely on both sides, said overlay being in the form of a prism tapering to a point towards said base of said posts.

5. A stent according to claim 4, wherein said posts have a trapezium cross-section with a shorter side, and a longer side opposite said shorter side, said shorter side of the trapezium being located axially outward of said longer side, said inner overlay adjoining the longer side of the trapezium, said triangular cross-section of said overlay having an apex pointing inward.

6. A stent according to claim 3, wherein said inner overlay tapers in cross-section from said backing surfaces, said overlay tapering at first triangularly or convexly on both sides and then triangularly or concavely on both sides, so that said web gradually deviates with small bending angles when it is closed, and is in addition supported by said inner overlay, said inner overlay tapering into the stent wall toward said bases of said posts.

7. A stent according to claim 3, wherein said posts are formed integrally with their respective inner overlays.

8. A stent according to claim 3, wherein said backing surfaces of said posts and said strips adjoin said outer wall of said stent forming an edge, said edge is rounded off.

9. A stent according to claim 3, wherein said backing surfaces of said strips and of said posts are singly curved between said inner and outer walls of said stent, said backing surfaces being inclined toward said outer wall of said stent.

10. A stent according to claim 3, wherein said bases of said posts have apertures, such that said posts and said strips connect to form a crown shape, said strips arching toward said base ring, said crown shape being connected to said base ring only by way of stays.

11. A stent according to claim 10, wherein said stay is vertical, said stay located under the base of each post.

12. A stent according to claim 10, wherein said stays are in the form of a V under the base of each post, each said post being connected to said base ring by way of two respective stays for the greatest possible flexibility with minimal pressure differentials.

13. A stent according to claim 3, wherein said stop means includes a coaxial stop ring in the region of said base ring.

14. A stent according to claim 13, wherein said stop ring and said base ring are integrally connected together.

15. A stent according to claim 13, wherein said stop ring has a circumferential groove.

16. A stent according to claim 15, wherein said outside wall of said stent has at least one at least partially circumferential lip, said lip located generally on said base of said post, said lip engaging said groove in said stop ring, said lip remaining freely movable within said groove.

17. A stent according to claim 16, wherein said bases of said posts have apertures, such that said posts and said strips connect to form a crown shape, said strips arching toward said base ring, said crown being connected to said base ring only by way of stays, said lip or lips provided on the outer wall of said stent, said lip or lips located on said stays.

18. A stent according to claim 13, wherein said curved strips and/or said stop ring have at least one at least partially circumferential recess, said recess or recesses associated in such a way that said ring serves as a stop for said strips.

19. A stent according to claim 3, wherein said stent has a diffuser shape.

20. A stent according to claim 19, wherein said stent has a conical shape opening toward said ends of said posts with cone angles between 20 and 140, the contraction of said stent into a cylindrical configuration being limited.

21. A stent according to claim 20, wherein the limit of the contractibility of the stent posts into the cylindrical configuration is reached at pressure differentials between 2 and 30 mm Hg.

22. A stent according to claim 3, wherein said webs having an arcuate rim, said rim having a triangular shaped edge, said edge engaging a corresponding recess in said backing surface.

23. A stent according to claim 3, wherein said webs having an arcuate, circumferential snap rim, said snap rim conforming with the outer surface of said stent.

24. A stent according to claim 1, wherein said backing surfaces of said posts and said strips adjoin said outer wall of said stent forming an edge and said edge is rounded off.

25. A stent according to claim 1, wherein said backing surfaces of said strips and of said posts are singly curved between said inner and outer walls of said stent, said backing surfaces being inclined toward said outer wall of said stent.

26. A stent according to claim 1, wherein said bases of said posts have apertures, such that said posts and said strips connect to form a crown shape, said strips arching toward said base ring, said crown shape being connected to said base ring only by way of stays.

27. A stent according to claim 26, wherein said stay is vertical, said stay located under the base of each post.

28. A stent according to claim 26, wherein said stays are in the form of a V under the base of each post, each said post being connected to said base ring by way of two respective stays for the greatest possible flexibility with minimal pressure differentials.

29. A stent according to claim 1 wherein, said stop means includes a coaxial stop ring in the region of said base ring.

30. A stent according to claim 29, wherein said stop ring and said base ring are integrally connected together.

31. A stent according to claim 29, wherein said stop ring has a circumferential groove.

32. A stent according to claim 31, wherein said outside wall of said stent has at least one at least partially circumferential lip, said lip located generally on said base of said post, said lip engaging said groove in said stop ring, said lip remaining freely movable within said groove.

33. A stent according to claim 32, wherein said bases of said posts have apertures, such that said posts and said strips connect to form a crown shape, said strips arching toward said base ring, said crown shape being connected to said base ring only by way of stays, said lip or lips provided on the outer wall of said stent, said lip or lips located on said stays.

34. A stent according to claim 29, wherein said curved strips and/or said stop ring have at least one at least partially circumferential recess, said recess or recesses associated in such a way that said ring serves as a stop for said strips.

35. A stent according to claim 1, wherein said stent has a diffuser shape.

36. A stent according to claim 35, wherein said stent has a conical shape opening toward said ends of said posts with cone angles between 2° and 14°, the contraction of said stent into a cylindrical configuration being limited.

37. A stent according to claim 36, wherein the limit of the contractibility of the stent posts into the cylindrical configuration is reached at pressure differentials between 2 and 30 mm Hg.

38. A stent according to claim 1, wherein said webs having an arcuate rim, said rim having a triangular shaped edge, said edge engaging a corresponding recess in said backing surface.

39. A stent according to claim 1, wherein said webs having an arcuate, circumferential snap rim, said snap rim conforming with the outer surface of said stent.

40. A stent according to claim 1, wherein said backing surfaces of said posts and said strips adjoin said outer wall of said stent forming an edge, said edge is rounded off.

41. A stent according to claim 1, wherein said backing surfaces of said strips and of said posts are singly curved between said inner and outer walls of said stent, said backing surfaces being inclined toward said outer wall of said stent.

* * * * *